US00PP15418P2

(12) United States Plant Patent
Olesen et al.

(10) Patent No.: US PP15,418 P2
(45) Date of Patent: Dec. 14, 2004

(54) ***CLEMATIS* PLANT NAMED 'EVIPO015'**

(50) Latin Name: *Clematis viticella*
Varietal Denomination: EVIpo015

(75) Inventors: Mogens N. Olesen, Fredensborg (DK); Raymond J. Evison, St. Sampsons (GB)

(73) Assignees: Poulsen Roser A/S, Fredensborg (DK); Raymond J. Evison Limited, Guernsey (GB)

( * ) Notice: Subject to any disclaimer, the term of this patent is extended or adjusted under 35 U.S.C. 154(b) by 0 days.

(21) Appl. No.: 10/756,048

(22) Filed: Jan. 12, 2004

(51) Int. Cl.[7] ..... A01H 5/00
(52) U.S. Cl. ..... Plt./228
(58) Field of Search ..... Plt./228

*Primary Examiner*—Kent Bell

(57) ABSTRACT

A new *Clematis* plant which is well suited to outdoor and indoor cultural methods, has exceptional tolerance to cold temperatures, displays profuse, light purple flowers, and demonstrates continuous summer flowering. The variety successfully propagates from softwood cuttings under normal glasshouse conditions and is suitable for cultivation in commercial glasshouses. This new and distinct variety has shown to be uniform and stable in the resulting generations from propagation.

1 Drawing Sheet

Variety denomination: 'EVIpo015'.
Botanical classification: Genus—*Clematis*. Species—*viticella*.
Commercial classification: Late Flowering Cultivar.

SUMMARY OF THE INVENTION

The present invention constitutes a new and distinct variety of *Clematis* which originated from a chance pollination between an unnamed female seed parent plant (unpatented) and an unknown male pollen parent plant.

The seed resulting from the chance pollination was germinated in a controlled environment. The new variety is named 'EVIpo015'.

The objective of the selection of this *Clematis* variety for commercial glasshouse and nursery culture was to create a new and distinct variety with unique qualities that this variety has:

1. Profusion of semi-nodding light purple flowers;
2. Long lasting flowers;
3. Non clinging habit;
4. Summer flowering;
5. Suitability for cultivation under glasshouse conditions;
6. Cold tolerant to USDA cold hardiness zone three.

These qualities required improvement in *Clematis* varieties that were in commercial cultivation and the objectives have been substantially achieved in the new variety, as evidenced by the unique combination of characteristics that are present in 'EVIpo015' which distinguish it from all other varieties of which we are aware. 'Evipo015' differs from its female parent primarily in flower color.

The seeds from the aforementioned chance pollination were germinated and evaluations of the resulting seedling plants were conducted in a controlled environment. As a result, 'EVIpo015' was selected by Raymond J. Evison and Mogens N. Olesen in their *Clematis* development program in Domarie Vineries Les Sauvagees, St. Sampsons, Guernsey, Channel Islands, United Kingdom in July of 1998.

Asexual reproduction of 'EVIpo015' by cuttings was first done by Raymond J. Evison and Mogens N. Olesen in Domarie Vineries Les Sauvagees, St. Sampsons, Guernsey, Channel Islands, United Kingdom in August 1998. This initial and subsequent propagations have demonstrated that the characteristics of 'EVIpo015' are true to type and are transmitted from one generation to the next.

BRIEF DESCRIPTION OF THE DRAWING

The accompanying color illustration show as true as is reasonably possible to obtain in color photographs of this type:

FIG. 1.1 Stem with juvenile growth;

FIG. 1.2 Mature stem showing attachment of mature leaves;

FIG. 1.3 Mature stem, petioloules, petioles, pedicels, bracts, and flower buds;

FIG. 1.4 Partially opened flowers attached to pedicel;

FIG. 1.5 Open flower, lower surface.

DETAILED DESCRIPTION OF THE VARIETY

The following is a detailed description of 'EVIpo015', as observed in its growth throughout the flowering period in glasshouses at Domarie Vineries Les Sauvagees, St. Sampsons, Guernsey, Channel Islands, United Kingdom. Observed plants were cultivated for a period of 24 months in 2 liter containers. Certain phenotypical characteristics of the variety may vary under different environmental, cultural, agronomic, seasonal, and climatic conditions. Color references are made using The Royal Horticultural Society (London, England) Colour Chart, 2001.

For a comparison, the nearest existing *Clematis* variety is 'Alionushka', non-patented. Chart 1 details several physical characteristics of the 'EVIpo015' and the comparison variety.

CHART 1

| | 'EvIpo015' | 'Alionushka' |
|---|---|---|
| Individual tepal length | 40 to 50 mm | 70 mm |
| Bracts | Small: 50 mm in length by 25 mm wide. | Large: 90 mm in length by 50 mm wide. |
| Flower abundance | Above average | Normal |

FLOWER AND FLOWER BUD

Blooming habit: Normally flowers from June through September.

Flower bud:

*Size.*—15 to 20 mm in length.

*Bud form.*—Ovoid.

*Bud color.*—Purple Group N79C at ¼ opening.

Peduncle:

*Surface.*—Smooth.

*Length.*—120 to 180 mm average length.

*Color.*—Green Group 137A.

*Strength.*—Moderately weak. Flowers are semi-nodding.

Receptacle: Flowers are attached directly to the peduncle.

Borne: In clusters, or compound dichasial cymes.

Flower bloom:

*Size.*—30 to 40 mm in diameter.

*Form.*—Upon opening, long campanulate, with tepals which reflex strongly.

*Color.*—Upon opening, the upper surface is Purple Group N78A. The lower side is Purple Group N78A. After opening, the upper surface is Purple Group N78A. The lower side is Purple Group N78A. General tonality is Purple Group N78A.

*Variations.*—None.

*Fragrance.*—None.

*Lasting quality on plant.*—7 to 10 days.

*Lasting quality as a cut flower.*—2 to 4 days.

Tepals:

*Quantity.*—Single. 4 on average.

*Shape.*—Individual tepal shape is elliptic.

*Cross section.*—Reflexed strongly.

*Margin.*—Entire with many small undulations along the length of the tepal.

*Tepal apex.*—Narrowly acute.

*Tepal base.*—Rounded.

*Recurvature of tip.*—Strongly recurved.

*Persistence.*—Tepals drop off cleanly.

*Arrangement.*—Tepals are arranged regularly.

Reproductive organs:

*Pollen.*—Quantity: Scant.

*Anthers.*—Length: 3 to 5 mm. Color: Yellow Group 13C. Arrangement: Regular.

*Filaments.*—Length: 5 to 10 mm. Color: Yellow-Green 144D.

*Stigmas.*—Totally enclosed by the anthers.

*Styles.*—Color: Green Group 136D to Yellow Group 11D.

PLANT

Plant form: Upright.

Plant growth: One season's growth attains 1.5 to 2 meters.

Hardiness: Trials to date show the variety hardy in USDA Zones 3–9.

Stems:

*Color.*—Young wood: Green Group 137C, turning to Greyed-Orange Group N170A. Older wood: Greyed-Orange Group 165C.

*Internodes.*—Shape: Cylindrical. Length: 90 mm.

*Bark.*—Young wood: Smooth. Older wood: Smooth.

Plant foliage: Deciduous. Compound leaves normally consist of 7 elliptic leaflets arranged in pinnate form.

*Leaf size.*—Typical leaflet size is approximately 30 to 40 mm in length, by 15 to 20 mm in width. Compound leaves are normally 200 mm in length by 100 mm wide.

*Abundance.*—Average.

*Color.*—New growth: Green Group 137C on upper and lower surfaces. Older growth: Upper surface is Green Group 137A. Lower surface is Green Group 137C.

Plant leaves and leaflets:

*Stipules.*—Absent.

*Petioloules.*—Length: 0 to 40 mm. Color: Green Group 137C. Characteristic: Non clasping.

*Petioles.*—Length: 30 to 60 mm. Color: Green Group 137C. Texture: Smooth. Characteristic: Non clasping.

*Leaflet edge.*—Terminal leaflet margin is entire.

*Leaflet shape.*—Base: Rounded to somewhat acute. Apex: Acute.

*Texture.*—Upper surface is glabrous with a matte appearance. Lower surface is veined with a matte appearance.

*Thickness.*—Thin.

Disease resistance: Subject to any disease that normally attacks the species, however the variety is more tolerant to Botrytis than other *Clematis* which we are aware of.

Cold tolerance: 'EVIpo015' has been found to be cold tolerant to USDA cold hardiness zone three.

We claim:

1. A new and distinct variety of *Clematis* plant named 'Evipo015', as illustrated and described herein as a distinct and novel *Clematis* variety due to its abundant light purple flowers with good keepability, exceptional cold hardiness, attractive long lasting foliage and compact growth, year round flowering under glasshouse conditions, suitability for production from softwood cuttings in pots, durable flowers and foliage which make the variety suitable for distribution in the floral industry.

* * * * *

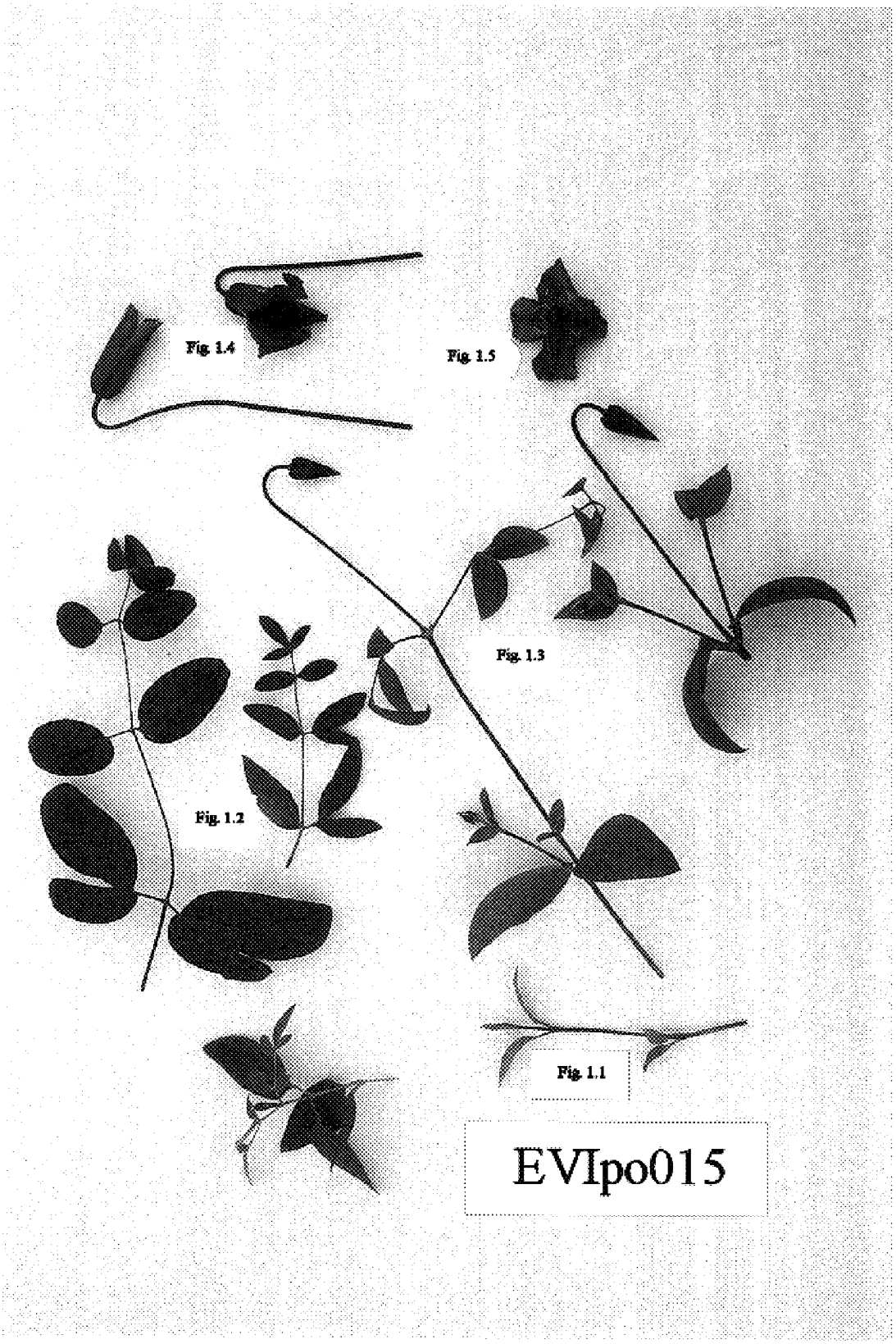
Fig. 1.4
Fig. 1.5
Fig. 1.3
Fig. 1.2
Fig. 1.1
EVIpo015